United States Patent [19]

Stanford et al.

[11] Patent Number: 5,885,588
[45] Date of Patent: Mar. 23, 1999

[54] *MYCOBACTERIUM VACCAE* FOR TREATMENT OF LONG TERM AUTOIMMUNE CONDITIONS

[75] Inventors: John Lawson Stanford, Claygate; Graham Arthur William Rook, Haverhill, both of United Kingdom

[73] Assignee: University College London, London, United Kingdom

[21] Appl. No.: 290,813

[22] PCT Filed: Feb. 19, 1993

[86] PCT No.: PCT/GB93/00351

§ 371 Date: Feb. 14, 1995

§ 102(e) Date: Feb. 14, 1995

[87] PCT Pub. No.: WO93/16727

PCT Pub. Date: Sep. 2, 1993

[30] Foreign Application Priority Data

Feb. 21, 1992 [GB] United Kingdom .................... 9203814

[51] Int. Cl.⁶ ..................................................... A61K 39/04
[52] U.S. Cl. ..................................... 424/248.1; 424/184.1; 424/197.11; 435/253.1
[58] Field of Search ............................... 424/248.1, 184.1, 424/197.11; 435/253.1; 530/822

[56] References Cited

U.S. PATENT DOCUMENTS

| 4,716,038 | 12/1987 | Standord et al. | 424/92 |
| 4,724,144 | 2/1988 | Rook et al. | 424/88 |

FOREIGN PATENT DOCUMENTS

| 8505034 | 11/1985 | WIPO . |
| 9102542 | 3/1991 | WIPO . |
| 9208488 | 5/1992 | WIPO . |
| 9102542 | 11/1995 | WIPO . |

*Primary Examiner*—James C. Housel
*Assistant Examiner*—Jennifer Shaver
*Attorney, Agent, or Firm*—IP Group of Pillsbury; Madison & Sutro LLP

[57] ABSTRACT

Antigenic and/or immunoregulatry material derived from *Mycobacterium vaccae* is useful in the treatment of mental diseases associated with an autoimmune reaction initiated by an infection and/or the auto immunologically mediated consequences (other than uveitis) of chronic infection.

8 Claims, No Drawings

MYCOBACTERIUM VACCAE FOR TREATMENT OF LONG TERM AUTOIMMUNE CONDITIONS

This invention relates to the treatment of mental diseases associated with an autoimmune reaction initiated by an infection, and of the auto-immunologically mediated consequences (other than uveitis) of chronic infections.

British Specification No. 2156673 describes immunotherapeutic agents comprising killed cells of *Mycobacterium vaccae*. These agents are useful in the immunotherapy of mycobacterial disease, especially tuberculosis and leprosy. It is stated that use of this immunotherapeutic agent facilitates the removal of the persisting bacilli responsible for tuberculosis or leprosy which, as is well known, it is difficult to remove by chemotherapy alone. It is suggested in the specification that the immunotherapeutic agent is believed to act by presenting the "protective " common mycobacterial antigens to advantage and by containing immune suppressor determinants which are active in regulating disadvantageous immune mechanisms. As a consequence, "persister " bacilli are recognised by the immune system by their content of common mycobacterial antigens and effective immune mechanisms are directed against them, in the absence of the tissue necrotic form of immunity usually present in mycobacterial disease.

International Patent Specification PCT/GB5/0013 describes compositions for the alleviation of the symptoms of, and for the treatment or diagnosis of, arthritic diseases which comprise as active ingredient the whole organism of *M. vaccae*. It is stated that the preparations of *M. vaccae* are useful for the treatment of various autoimmune diseases and especially arthritic conditions including rheumatoid arthritis, ankylosing spondylitis or Reiter's syndrome.

International Patent Specification PCT/GB90/0131 discloses that compositions which comprise *M. vaccae* as active ingredient are useful in the treatment of other pathological conditions in which the patient shows an abnormally high proportion of agalactosyl IgG and also in the treatment of chronic inflammatory disorders caused or accompanied by an abnormally high release by macrophages of interleukin-6 and/or tumour necrosis factor. The specification refers in particular to the treatment of Crohn's disease, reactive arthritis, primary biliary cirrhosis, sarcoidosis, ulcerative colitis, psoriasis, systemic lupus erythematosus (especially when accompanied by Sjogren's syndrome), multiple sclerosis, Guillain-Barre syndrome, primary diabetes mellitus, and some aspects of graft rejection.

International Patent Specification PCT/GB90/01169 discloses antigenic and/or immunoregulatory material derived from *M. Vaccae* for use in delaying or preventing the onset of the AIDS syndrome.

Additionally, our unpublished International Patent Specification PCT/GB91/01970 discloses the use of *M. vaccae* in the treatment of uveitis, an immunologically mediated late consequence of leprosy, which causes blindness.

The present invention is based on the surprising, observation that *M. vaccae* is also effective against a number of other conditions which may involve infections such as bacterial or protozoan infections and in particular mycobacterial infections.

It has been suggested that mental diseases such as schizophrenia and manic depression are associated with an autoimmune reaction resulting from past or on-going cryptic infection. Evidence for this is provided by abnormal B and T lymphocyte function such as increased B cells, decreased T cells and altered suppressor cell levels which have been observed in schizophrenia (see for example P. Sirota, Israel J. Med. Sci, 1990, 26, 694–697; J. G. Knight, Meth and Find Exptl Clin; Pharmacol., 1984, 64, 395–403; H. H. Fudenberg et al, Biomedicine & Pharmacotherapy, 1984, 38, 285–290; F. Villemain et al, Annal. N.Y. Acad. Sci., 1987, 496, 669–675; and Ganguli et al, Annal. N.Y. Acad. Sci., 1987, 496, 676–685). Evidence is also provided by the observation that schizophrenia and rheumatoid arthritis almost never occur in the same patient (T. D. Spector, J. Silman, Brit. J. Rheumatology, 1987, 26, 307–310). We believe that schizophrenia and rheumatoid arthritis may be caused by genetically determined, mutually exclusive, reactions to cryptic infection and probably mycobacterial infection. In a limited trial we have found that three out of three patients suffering from schizophrenia have shown a dramatic improvement when treated with *M. vaccae*. We therefore believe *M. vaccae* may be useful in treating mental diseases associated with an autoimmune reaction.

We have also found that *M. vaccae* is effective in the treatment of the immunologically mediated consequences of chronic infections.

Chaga's disease (South American Trypanosomiasis) is an example of a disease associated with a protozoan infection a late consequence of which is myocarditis which normally leads to the death of a patient. Treatment with *M. vaccae* may reduce the incidence of myocarditis.

Another example of such a disease is Takayasu's arteritis which is associated with tuberculosis which is caused by mycobacterial infection. It is believed that this and other vascular diseases including obstructive vascular diseases, which may be immunologically mediated, may be prevented and treated with *M. vaccae*.

It is also believed that *M. vaccae* may be effective in the prophylaxis and treatment of vascular complications associated with diabetes, which may be immunologically mediated.

The present invention accordingly provides a method for the treatment of a mental disease associated with an autoimmune reaction which may have been initiated by an infection, for the treatment of the immunologically mediated consequences of Chaga's disease, or for the prophylaxis or treatment of vascular diseases or complications which may be immunologically mediated such as those associated with tuberculosis or diabetes which comprises administering to the patient suffering from such a condition an effective amount of a therapeutic composition comprising antigenic and immunoregulatory material derived from *Mycobacterium vaccae*.

The invention further provides antigenic and immunoregulatory material derived from *M. vaccae* for use in the manufacture of a therapeutic agent for the treatment of a mental disease associated with an autoimmune reaction which may have been initiated by an infection, for the treatment of the immunologically mediated consequences of Chaga's disease, or for the prophylaxis or treatment of vascular diseases or complications which may be immunologically mediated such as those associated with tuberculosis or diabetes.

The present invention is in particular directed to treatment of bacterial or protozoan infections, for example mycobacterial infections.

Preferably the antigenic or immunoregulatory material is for use in the treatment of a mental disease associated with an autoimmune reaction initiated by an infection, such as a mycobacterial infection. Such an infection may be a past infection which triggers an autoimmune response. Alternatively the autoimmune response may be initiated by an ongoing infection, such as a mycobacterial infection, which is cryptic, i.e. not readily detectable.

The therapeutic agent of the invention conveniently, and therefore preferably, comprises dead cells of *M. vaccae*, most preferably cells which have been killed by autoclaving or by irradiation. The therapeutic agent normally comprises more than $10^8$ microorganisms per ml of diluent, and preferably from $10^8$ to $10^{11}$ killed *M. vaccae* microorganisms per ml of diluent.

The diluent may be pyrogen-free saline for injection alone, or a borate buffer of pH 8.0. The diluent should be sterile. A suitable borate buffer is:

| | |
|---|---|
| $Na_2B_4O_7.10H_2O$ | 3.63 g |
| $H_3BO_3$ | 5.25 g |
| NaCl | 6.19 g |
| Tween 80 | 0.0005% |
| Distilled Water | to 1 liter |

The preferred strain of *M. vaccae* is one denoted R877R isolated from mud samples from the Lango district of Central Uganda (J. L. Stanford and R. C. Paul, Ann. Soc. Belge Med, Trop. 1973, 53 141–389). The strain is a stable rough variant and belongs to the aurum sub-species. It can be identified as belonging to *M. vaccae* by biochemical and antigenic criteria (R. Bonicke, S. E. Juhasz., Zentr albl. Bakteriol. Parasitenkd. Infection skr. Hyg. Abt. 1, Orig., 1964, 192, 133. The strain denoted R877R has been deposited under the Budapest Convention at the National Collection of Type Cultures (NCTC) Central Public Health Laboratory, Colindale Avenue, London NW9 5HT, United Kingdom on Feb. 13th, 1984 under the number NCTC 11659.

For the preparation of the therapeutic agent, the microorganism *M. vaccae* may be grown on a suitable solid medium. A modified Sauton's liquid medium is preferred (S. V. Boyden and E. Sorkin., J. Immuno, 1955 75, 15) solidified with agar. Preferably the solid medium contains 1.3% agar. The medium inoculated with the microorganisms is incubated aerobically to enable growth of the microorganisms to take place, generally at 32° C. for 28 days. The organisms are harvested, then weighed and suspended in a diluent. The diluent may be unbuffered saline but is preferably borate-buffered and contains a surfactant such as Tween 80 as described above. The suspension is diluted to give 100 mg of microorganism/ml. For further dilution, borate buffered saline is preferably used so that the suspension contains 10 mg wet weight of microorganisms/ml in multidose vials. Although the microorganisms in the vials may be killed using irradiation e.g. from $^{60}$Cobalt at a dose of 2.5 megarads, or by any other means, for example chemically, it is preferred to kill the microorganisms by autoclaving, for example at 15 psi (103.5 kPa) for 15 minutes (115°–125° C.). It has been discovered that autoclaving yields a more effective preparation than irradiation.

The therapeutic agent is in general administered by injection in a volume in the range 0.1–0.2 ml, preferably 0.1 ml given intradermally. A single dosage will generally contain from $10^7$ to $10^{10}$ killed *M. vaccae* microorganisms. It is preferred to administer to patients a single dose containing $10^8$ to $10^9$ killed *M. vaccae*. A single dose may be administered or the dose may be repeated depending on the condition of the patient.

Although the therapeutic agent will generally be administered by intradermal injection, other routes, e.g. oral administration, can also be used.

It may be advantageous and is within the scope of the invention to use more than one strain of *M. vaccae*, and/or to include in the antigenic on immunoregulatory material other closely related mycobacterial species, such as *M. nonchromogenicum* or *M. chitae*. Tuberculin may also be included.

The therapeutic agent can contain further ingredients such as adjuvants, preservatives, stabilisers etc. It may be supplied in sterile injectable liquid form or in sterile freeze-dried form which is reconstituted prior to use.

*M. vaccae* may be used as such or an extract or fractioned portion of the organism to manufacture the therapeutic agents according to the invention.

The following Example illustrates the invention.

EXAMPLE

*M. vaccae* NCTC 11659 is grown on a solid medium comprising modified Sauton's medium solidified with 1.3% agar. The medium is inoculated with the microorganism and incubated for 28 days at 32° C. to enable growth and maturation of the microorganism to take place. The microorganisms are then harvested by gently scraping the surface of the agar and weighed (without drying) and suspended in M/15 borate buffered saline at pH 8 to give 10 mg of microorganisms/ml of saline. The suspension is dispensed into 5 ml vials, and then autoclaved for 15 minutes at 15 psi (103.5 kPa) to kill the microorganisms. After cooling, the therapeutic agent thus produced is stored at 4° C. before use. A single dose consists of 0.1 ml of the suspension, which should be shaken vigorously immediately before use, containing 1 mg wet weight of *M. vaccae*. The dose is given by intradermal injection normally over the left deltoid muscle.

We claim:

1. A method for the treatment of schizophrenia associated with an autoimmune reaction initiated by an infection, said method comprising administering by injection, to a patient suffering from such disease a therapeutic agent comprising dead cells of *Mycobacterium vaccae* in an amount effective to ameliorate the disease.

2. The method according to claim 1, wherein the cells of *M. vaccae* have been killed by autoclaving.

3. The method according to claim 1, wherein the therapeutic agent is derived from the strain of *M. vaccae* deposited at the National Collection of Type Cultures (NCTC) Central Public Health Laboratory, Colindale Avenue, London NW9 4HT, United Kingdom on Feb. 13th, 1984 under the number NCTC 11659.

4. The method according to claim 1, wherein the therapeutic agent contains, per dose, from $10^7$ to $10^{10}$ *M. vaccae* microorganisms.

5. A method for the prophylaxis or treatment of an immunologically-mediated cardiovascular condition caused by an autoimmune reaction, which condition is selected from the vascular aspects of leprosy and the vascular aspects of chronic myocarditis induced by *T. cruzi*, said method comprising administering by injection to a patient suffering from such condition a therapeutic agent comprising dead cells of *Mycobacterium vaccae* in an amount effective to ameliorate the condition.

6. The method according to claim 5, wherein the cells of *M. vaccae* have been killed by autoclaving.

7. The method according to claim 5, wherein the therapeutic agent contains, per dose, from $10^7$ to $10^{10}$ *M. vaccae* microorganisms.

8. The method according to claim 5, wherein the therapeutic agent is derived from the strain of *M. vaccae* deposited at the National Collection of Type Cultures (NCTC) Central Public Health Laboratory, Colindale Avenue, London NW9 4HT, United Kingdom on Feb. 13th, 1984 under the number NCTC 11659.

* * * * *